(12) United States Patent
Smith et al.

(10) Patent No.: US 11,267,772 B2
(45) Date of Patent: *Mar. 8, 2022

(54) PROCESS FOR THE PREPARATION OF 2,3,3,3-TETRAFLUOROPROPENE

(71) Applicant: MEXICHEM AMANCO HOLDING S.A. DE C.V., Tlalnepantla (MX)

(72) Inventors: John W Smith, Cheshire (GB); Claire McGuinness, Cheshire (GB); Andrew P Sharratt, Cheshire (GB); Andrew M Taylor, Chester (GB)

(73) Assignee: MEXICHEM AMANCO HOLDING S.A. DE C.V., Tlalnepantla (MX)

( * ) Notice: Subject to any disclaimer, the term of this patent is extended or adjusted under 35 U.S.C. 154(b) by 0 days.

This patent is subject to a terminal disclaimer.

(21) Appl. No.: 16/896,758

(22) Filed: Jun. 9, 2020

(65) Prior Publication Data

US 2020/0325089 A1   Oct. 15, 2020

Related U.S. Application Data

(63) Continuation of application No. 15/960,860, filed on Apr. 24, 2018, now Pat. No. 10,683,248, which is a continuation of application No. 14/876,090, filed on Oct. 6, 2015, now Pat. No. 9,957,210, which is a continuation of application No. 12/992,637, filed as application No. PCT/GB2009/001263 on May 15, 2009, now Pat. No. 9,162,948.

(30) Foreign Application Priority Data

May 15, 2008   (GB) ..................... 0808836

(51) Int. Cl.
C07C 17/25    (2006.01)
C07C 17/354   (2006.01)
C07C 21/18    (2006.01)

(52) U.S. Cl.
CPC ............ *C07C 17/25* (2013.01); *C07C 17/354* (2013.01); *C07C 21/18* (2013.01)

(58) Field of Classification Search
None
See application file for complete search history.

(56) References Cited

U.S. PATENT DOCUMENTS

| | | | |
|---|---|---|---|
| 2,931,840 A | 4/1960 | Maley | |
| 5,315,048 A * | 5/1994 | Van Der Puy | C07C 17/23 570/151 |
| 5,396,000 A | 3/1995 | Nappa et al. | |
| 5,679,875 A | 10/1997 | Aoyama et al. | |
| 6,031,141 A | 2/2000 | Mallikarjuna et al. | |
| 6,329,559 B1 * | 12/2001 | Sievert | C07C 17/00 570/164 |
| 6,369,284 B1 * | 4/2002 | Nappa | B01J 21/18 570/156 |
| 6,548,719 B1 | 4/2003 | Nair et al. | |
| 7,897,823 B2 | 3/2011 | Miller et al. | |
| 9,162,948 B2 * | 10/2015 | Smith | C07C 17/354 |
| 9,957,210 B2 * | 5/2018 | Smith | C07C 17/25 |
| 10,683,248 B2 * | 6/2020 | Smith | C07C 17/25 |
| 2005/0245773 A1 * | 11/2005 | Mukhopadhyay | C07C 17/278 570/155 |
| 2007/0100175 A1 | 5/2007 | Miller et al. | |
| 2007/0123741 A1 | 5/2007 | Van der Puy et al. | |
| 2007/0179324 A1 | 8/2007 | Van der Puy et al. | |
| 2008/0051611 A1 | 2/2008 | Wang et al. | |
| 2009/0234165 A1 | 9/2009 | Chiu et al. | |
| 2010/0305370 A1 | 12/2010 | Devic et al. | |

FOREIGN PATENT DOCUMENTS

| | | |
|---|---|---|
| EP | 0502605 | 9/1992 |
| EP | 0658531 | 6/1995 |
| EP | 0773061 | 5/1997 |
| EP | 0957074 | 11/1999 |
| EP | 982281 | 3/2000 |
| EP | 1350564 | 10/2003 |
| EP | 2100867 | 9/2009 |
| EP | 2213642 | 8/2010 |
| EP | 2289865 | 3/2011 |
| EP | 2292574 | 3/2011 |
| JP | 08165256 | 6/1996 |
| JP | 08169851 | 7/1996 |
| JP | 9095459 | 4/1997 |
| JP | 2009-221202 | 10/2009 |
| WO | WO90/08750 | 9/1990 |
| WO | WO94/27940 | 12/1994 |
| WO | WO1996/016922 | 6/1996 |
| WO | WO98/10862 | 3/1998 |
| WO | WO98/33755 | 8/1998 |
| WO | WO98/33756 | 8/1998 |
| WO | WO2005/012212 | 2/2005 |
| WO | WO 2005/108334 | 11/2005 |
| WO | WO2006/106353 | 10/2006 |
| WO | WO2007/019355 | 2/2007 |
| WO | WO2007/086972 | 8/2007 |
| WO | WO2007/117391 | 10/2007 |
| WO | WO2008/002501 | 1/2008 |

(Continued)

OTHER PUBLICATIONS

Knunyants et al., Russ. Chem. Bull., 1958, p. 884.

(Continued)

*Primary Examiner* — Clinton A Brooks
(74) *Attorney, Agent, or Firm* — Crowell & Moring LLP

(57) ABSTRACT

The invention provides a process for the preparation of 1234yf comprising (a) contacting 1,1,2,3,3,3-hexafluoropropene (1216) with hydrogen in the presence of a hydrogenation catalyst to produce 1,1,2,3,3,3-hexafluoropropane (236ea); (b) dehydrofluorinating 236ea to produce 1,2,3,3,3-pentafluoropropene (1225ye); (c) contacting 1225ye with hydrogen in the presence of a hydrogenation catalyst to produce 1,2,3,3,3-pentafluoropropane (245eb); and (d) dehydrofluorinating 245eb to produce 1234yf.

18 Claims, 3 Drawing Sheets

(56) References Cited

FOREIGN PATENT DOCUMENTS

| WO | WO2008/030439 | 3/2008 |
|----|---------------|--------|
| WO | WO2008/030440 | 3/2008 |
| WO | WO2008030440 | 3/2008 |
| WO | WO 2008/040969 | 4/2008 |
| WO | WO2008/084703 | 7/2008 |
| WO | WO2009/084703 | 7/2009 |
| WO | WO2009/084730 | 7/2009 |
| WO | WO2009/093047 | 7/2009 |
| WO | WO 2009/137656 | 11/2009 |
| WO | WO2009/153492 | 12/2009 |
| WO | WO2009/153493 | 12/2009 |

OTHER PUBLICATIONS

Knunyants et al. Russ. Chem. Bull., 1960, pates 1312-1317.
Banks et al., J. Fluorine Chem., (82) 1997, pp. 171-174.
International Preliminary Report on Patentability regarding International Appln. No. PCT/GB2009/001263 dated Nov. 25, 2010, 5 pgs.

* cited by examiner

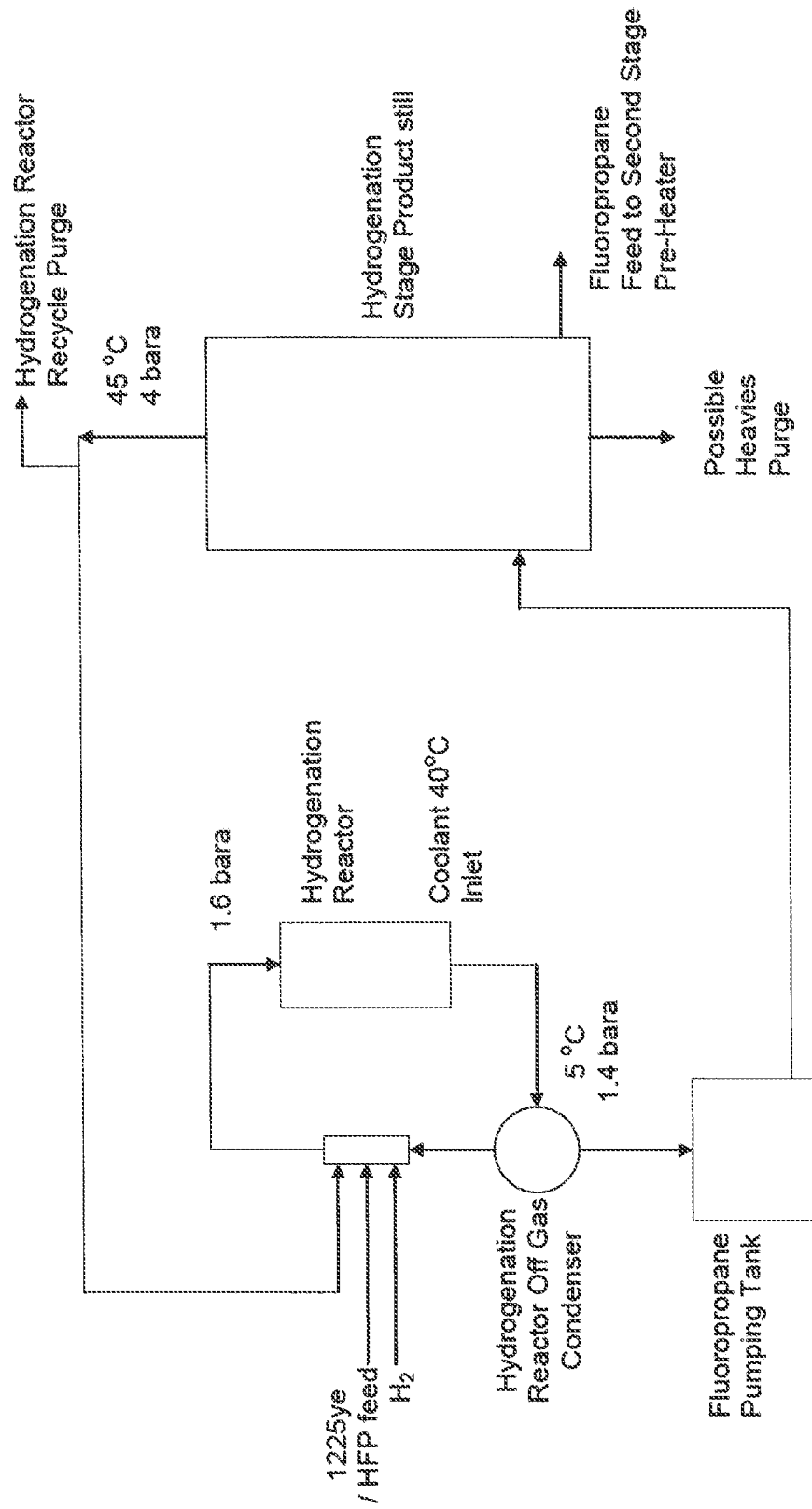
Figure 1: Hydrogenation stage

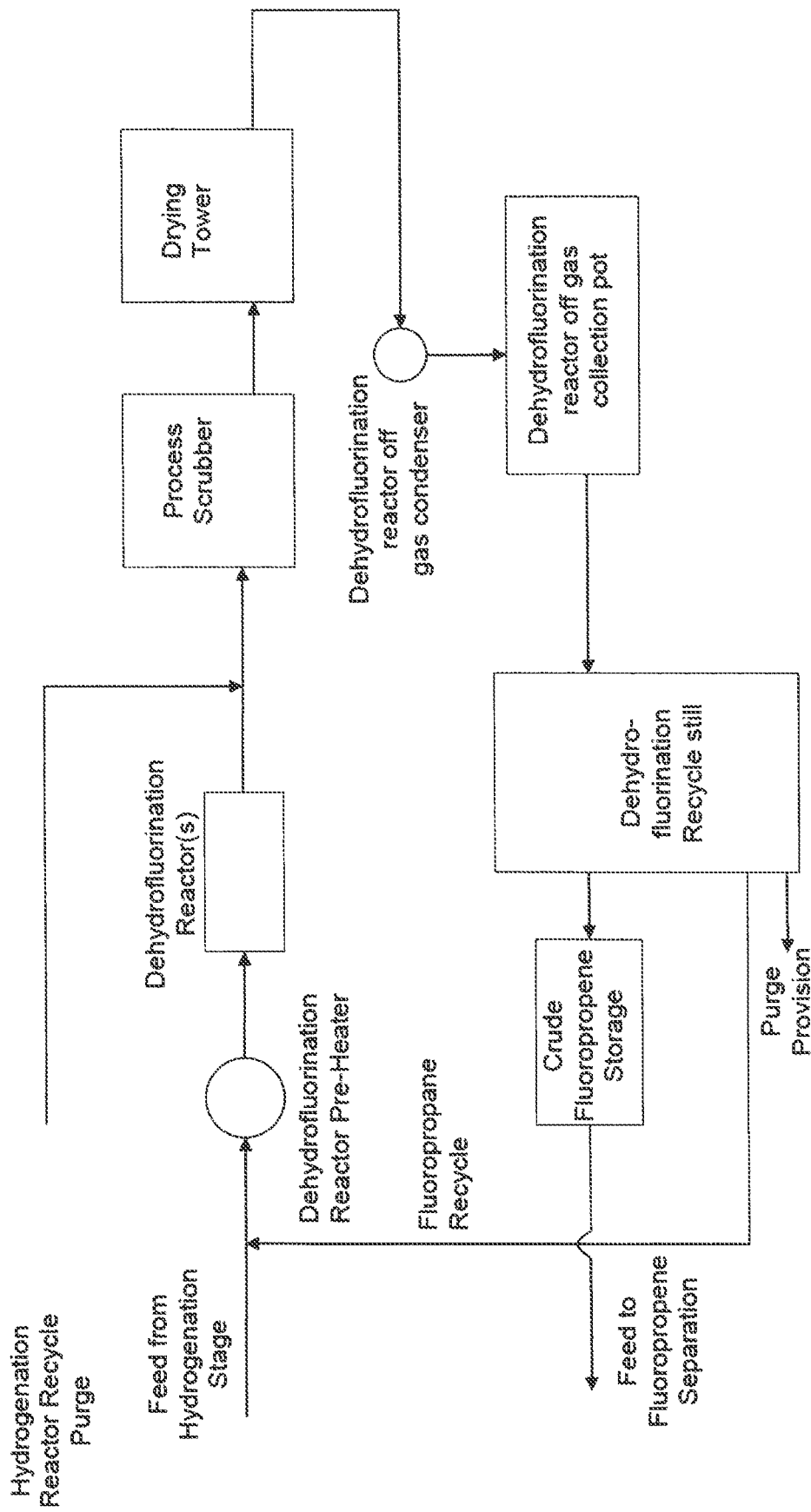
Figure 2: Dehydrofluorination stage

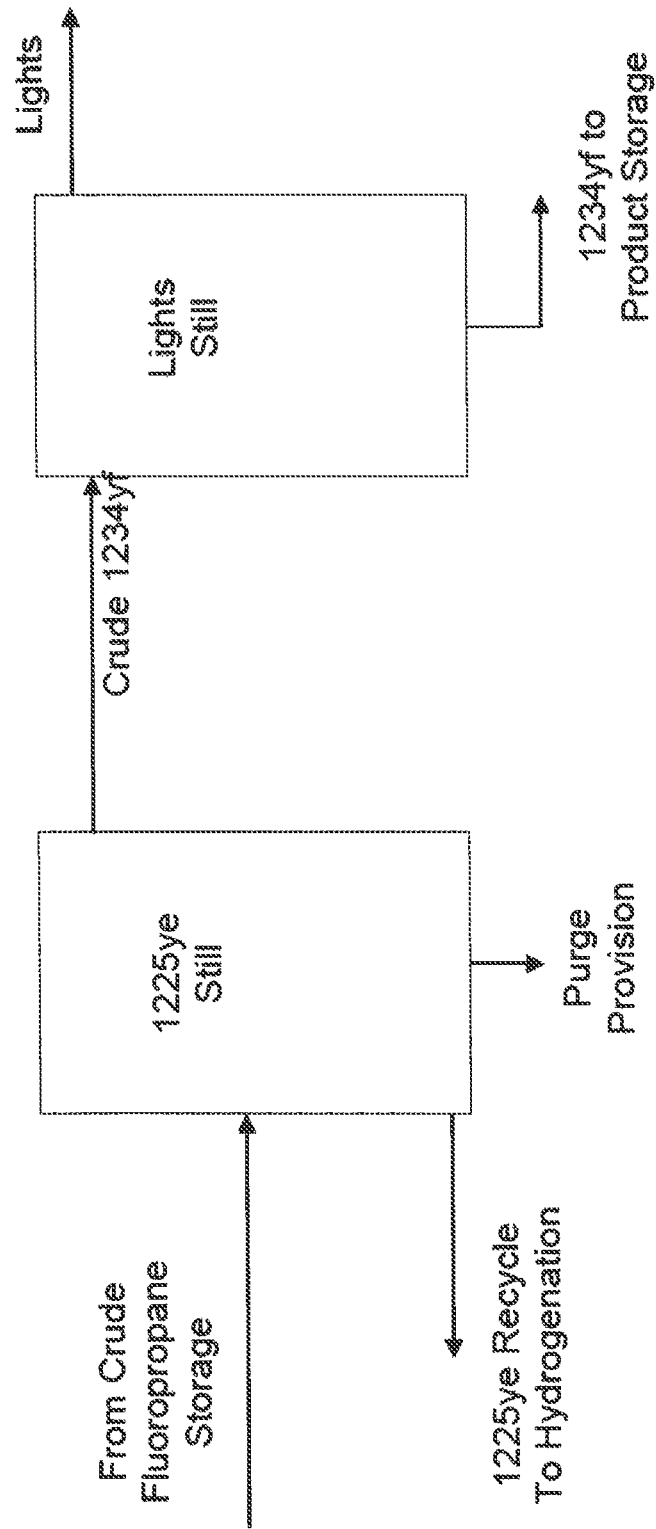

PROCESS FOR THE PREPARATION OF 2,3,3,3-TETRAFLUOROPROPENE

RELATED APPLICATIONS

This application is a continuation of U.S. patent application Ser. No. 15/960,860 filed 24 Apr. 2018 (now U.S. Pat. No. 10,683,248), which is a continuation of U.S. patent application Ser. No. 14/876,090 filed 6 Oct. 2015 (now U.S. Pat. No. 9,957,210), which is a continuation of application Ser. No. 12/992,637, filed 21 Jan. 2011 (now U.S. Pat. No. 9,162,948), which was a U.S. National Phase entry under 35 U.S.C. § 371 of International Application Serial No. PCT/GB09/01263, filed 15 May 2009, which claimed the benefit of Great Britain Application Serial No. 0808836.1, filed 15 May 2008.

BACKGROUND OF THE INVENTION

The invention relates to a process for the preparation of 2,3,3,3-tetrafluoropropene.

2,3,3,3-tetrafluoropropene is also known as HFO-1234yf, HFC-1234yf or simply 1234yf. Hereinafter, unless otherwise stated, 2,3,3,3-tetrafluoropropene will be referred to as 1234yf. The known processes for preparing 1234yf typically suffer from disadvantages such as low yields, and/or the handling of toxic and/or expensive reagents, and/or the use of extreme conditions, and/or the production of toxic by-products.

Methods for the preparation of 1234yf have been described in, for example, Journal Fluorine Chemistry (82), 1997, 171-174. In this paper, 1234yf is prepared by the reaction of sulphur tetrafluoride with trifluoroacetylacetone. However, this method is only of academic interest because of the hazards involved in handling the reagents and their expense.

Another method for the preparation of 1234yf is described in U.S. Pat. No. 2,931,840. In this case, pyrolysis of C1 chlorofluorocarbons with or without tetrafluoroethylene was purported to yield 1234yf. However, the yields described were very low and again it was necessary to handle hazardous chemicals under extreme conditions. It would also be expected that such a process would produce a variety of very toxic by-products.

In addition to addressing the disadvantages of the known methods, it would be desirable to provide a new method for the preparation of 1234yf that use only readily available feedstocks.

The listing or discussion of a prior-published document in this specification should not necessarily be taken as an acknowledgement that the document is part of the state of the art or is common general knowledge.

SUMMARY OF THE INVENTION

The subject invention addresses the deficiencies of the known methods for preparing 1234yf by providing a process for the preparation of 1234yf comprising (a) contacting 1,1,2,3,3,3-hexafluoropropene (referred to hereinafter as 1216 or HFP) with hydrogen in the presence of a hydrogenation catalyst to produce 1,1,2,3,3,3-hexafluoropropane (referred to hereinafter as 236ea); (b) dehydrofluorinating 236ea to produce 1,2,3,3,3-pentafluoropropene (referred to hereinafter as 1225ye); (c) contacting 1225ye with hydrogen in the presence of a hydrogenation catalyst to produce 1,2,3,3,3-pentafluoropropane (referred to hereinafter as 245eb); and (d) dehydrofluorinating 245eb to produce 1234yf. Unless otherwise stated, this will be known hereinafter as the process of the invention.

1225ye exists as the geometric isomers E-1225ye and Z-1225ye. Unless otherwise stated, as used herein, 1225ye shall refer to a mixture of the geometric isomers.

Each of steps (a) to (d) may be carried out batch-wise or continuously (preferably continuously), using any suitable apparatus, such as a static mixer, a tubular reactor, a stirred tank reactor or a stirred vapour-liquid disengagement vessel. Preferably, the apparatus is made from one or more materials that are resistant to corrosion, e.g. Hastelloy® or Inconel®.

BRIEF DESCRIPTION OF THE DRAWINGS

FIG. 1 is a schematic drawing of a hydrogenation stage used in the present invention.

FIG. 2 is a schematic drawing of a dehydrofluorination stage used in the present invention.

FIG. 3 is a schematic drawing depicting purification of R-1225ye and R-1234yf according to the present invention.

DESCRIPTION OF THE PREFERRED EMBODIMENT

In any of the aspects of the process of the invention described herein, the products from step (a), (b), (c) and/or (d) may be subjected to a purification step. The purification may be achieved, for example, by separation of the desired product(s) or reagents by one or more distillation, condensation or phase separation steps and/or by scrubbing with water or aqueous base.

The process of the invention may be carried out using a variety of suitable reactor topologies. For example, the process may be carried out continuously with steps (a), (b), (c) and (d) being conducted sequentially in that order using a separate reactor for each step.

Alternatively, the process may be carried out in a semi-batch manner using one hydrogenation reactor and one dehydrofluorination reactor, and with steps (a), (b), (c) and (d) being conducted sequentially in that order. In such a semi-batch process, HFP is converted to 236ea in the hydrogenation reactor and the 236ea is converted to 1225ye in the dehydrofluorination reactor. Both of these reactions, steps (a) and (b), are carried out for a defined period, typically from about 1 to about 1000 hours, such as from about 10 to about 500 hours, e.g. from about 20 to about 200 hours. The 1225ye produced is stored in a buffer tank before the same hydrogenation and dehydrofluorination reactors are used to convert 1225ye to 245eb and 245eb to 1234yf, respectively. Again, these reactions, steps (c) and (d), are carried out for a defined period, typically from about 1 to about 1000 hours, such as from about 10 to about 500 hours, e.g. from about 20 to about 200 hours.

In a further preferred reaction topology, steps (a) and (c) of the process of the invention may be carried out simultaneously in the same reactor. The hydrogenation of fluoroolefins such as HFP and 1225ye is known to be highly exothermic. By combining the hydrogenation reactions it is thought that the exothermic nature of the reactions can be controlled by taking advantage of the different heats of reaction and heat capacities of the products. This has the advantages of lower capital cost and increased efficiency for the process of the invention.

The product of the reaction wherein steps (a) and (c) are conducted simultaneously in the same reactor comprises both 236ea and 245eb. These may be separated from each other (e.g. by distillation) before being fed into separate dehydrofluorination reactors for carrying out steps (b) and (d).

Alternatively, following any optional purification step(s) to remove unwanted by-products (e.g. CF3CFHCH3 (254eb) and/or H2), a combined stream of 236ea and 245eb may be fed to a single reactor. Thus, dehydrofluorination steps (b) and (d) may be carried out simultaneously in the same reactor. This is believed to have the advantages of lower capital cost and increased efficiency for the process of the invention. Of course, separate feeds of 236ea and 245eb originating from separate hydrogenation reactors may be fed to a single dehydrofluorination reactor in which steps (b) and (d) are carried out simultaneously.

In a yet further embodiment, the exothermic hydrogenation reactions of step (a) and/or (c), particularly step (a), may be controlled by the use of a diluent gas stream. For the avoidance of doubt, a diluent gas stream can be used for step (a) alone, step (c) alone or steps (a) and (c) combined. The diluent gas stream can be a gas such as nitrogen or 1,1,1,2-tetrafluoroethane (134a), an excess of one or more of the feedstocks (e.g. HFP and/or 1225ye), or indeed one or both of the products from steps (a) and (c), 245eb or 236ea.

The following description of the preferred conditions, catalyst etc. for steps (a) and (c) is applicable to all the reactor topologies (e.g. those described above) which may be used to carry out the process of the invention.

The hydrogenation reactions in step (a) and (c) may be carried out in the liquid or vapour phase, preferably the vapour phase. A temperature of from about −50 to about 275° C. may be used for steps (a) and (c). Preferred temperatures for liquid phase hydrogenation are from about −50 to about 50° C., e.g. from about 15 to about 40° C. Preferred temperatures for vapour phase hydrogenation are from about 0 to about 250° C., such as from about 20 to about 200° C., e.g. from about 50 to about 150° C.

Steps (a) and (c), may be carried out in the presence of a fluorinated polar aprotic solvent, particularly when carried out in the liquid phase. Suitable solvents include HFCs (e.g. 134a) and PFCs (e.g. perfluorodecalin).

The hydrogenation reactions in step (a) and (c) may be carried out at atmospheric, sub- or super-atmospheric pressure, preferably super-atmospheric pressure. For example, the hydrogenation may be carried out at a pressure of from about 0 to about 40 bara, such as from about 1 to about 30 bara, e.g. from about 5 to about 20 bara.

The ratio of hydrogen:1216 in step (a) and hydrogen: 1225ye in step (c) is suitably from about 0.1:1 to about 40:1, such as from about 1:1 to about 20:1, preferably, from about 1.1:1 to about 10:1, e.g. from about 1.5:1 to about 5:1.

Any suitable hydrogenation catalyst may be used in steps (a) and (c), including catalysts comprising a transition metal. Preferred transition metal hydrogenation catalysts include those comprising Ni, Pd, Pt, Re, Rh, Ru and mixtures thereof. Such catalysts may be supported (e.g. on alumina, titania, silica, zirconia (or fluorides of the foregoing), calcium fluoride, carbon or barium sulphate) or unsupported (e.g. Raney Ni or palladium sponge). Palladium supported on carbon (Pd/C) currently is a preferred hydrogenation catalyst for steps (a) and (c).

The hydrogenation catalyst typically is used in an amount of from about 0.01 to about 30% by weight based on the total weight of the components which make up steps (a) and (c), such as from about 0.1 to about 10%. When Pd/C is used as the catalyst, the Pd is present in an amount of from about 0.01 to about 10% by weight of the catalyst, such as from about 0.1 to about 5%.

The contact time for the hydrogen and catalyst with 1216 and 1225ye in steps (a) and (c) suitably is from about 1 to about 200 seconds, such as from about 2 to about 150 seconds.

The following description of the preferred conditions, reagents, catalyst etc. for steps (b) and (d) is applicable to all the reactor topologies (e.g. those described hereinbefore) which may be used to carry out the process of the invention.

Steps (b) and (d) of the process of the invention may be carried out under any suitable reaction conditions effective to dehydrofluorinate 236ea to produce 1225ye and/or 245eb to produce 1234yf. The dehydrofluorination may be carried out in the vapour or liquid phase and at a temperature of from about −70 to about 1000° C. (e.g. about 0 to about 400° C.). The process may be carried out at atmospheric, sub- or super-atmospheric pressure, preferably from about 0 to about 30 bara.

The dehydrofluorination may be induced thermally, may be base-mediated and/or may be catalysed by any suitable catalyst. Suitable catalysts include metal and carbon based catalysts such as those comprising activated carbon, main group (e.g. alumina-based catalysts) and transition metals, such as chromia-based catalysts (e.g. zinc/chromia) or nickel-based catalysts (e.g. nickel mesh).

One preferred method of effecting the dehydrofluorination in steps (b) and (d) is by contacting 236ea and 245eb with a catalyst based on chromia such as those described in EP-A-0502605, EP-A-0773061, EP-A-957074, WO 98/10862 and WO 2006/106353 (e.g. a zinc/chromia catalyst).

By the term "zinc/chromia catalyst" we mean any catalyst comprising chromium or a compound of chromium and zinc or a compound of zinc. Typically, the chromium or compound of chromium present in the zinc/chromia catalysts of the invention is an oxide, oxyfluoride or fluoride of chromium such as chromium oxide.

The total amount of the zinc or a compound of zinc present in the zinc/chromia catalysts of the invention is typically from about 0.01% to about 25%, preferably 0.1% to about 25%, conveniently 0.01% to 6% zinc, and in some embodiments preferably 0.5% by weight to about 25% by weight of the catalyst, preferably from about 1 to 10% by weight of the catalyst, more preferably from about 2 to 8% by weight of the catalyst, for example about 4 to 6% by weight of the catalyst. In other embodiments, the catalyst conveniently comprises 0.01% to 1%, more preferably 0.05% to 0.5% zinc.

The preferred amount depends upon a number of factors such as the nature of the chromium or a compound of chromium and/or zinc or a compound of zinc and/or the way in which the catalyst is made. These factors are described in more detail hereinafter.

It is to be understood that the amount of zinc or a compound of zinc quoted herein refers to the amount of elemental zinc, whether present as elemental zinc or as a compound of zinc.

The zinc/chromia catalysts used in the invention may include an additional metal or compound thereof. Typically, the additional metal is a divalent or trivalent metal, preferably selected from nickel, magnesium, aluminium and mixtures thereof. Typically, the additional metal is present in an amount of from about 0.01% by weight to about 25% by weight of the catalyst, preferably from about 0.01 to 10% by weight of the catalyst. Other embodiments may comprise at least about 0.5% by weight or at least about 1% weight of additional metal.

The zinc/chromia catalysts used in the present invention may be amorphous. By this we mean that the catalyst does not demonstrate substantial crystalline characteristics when analysed by, for example, X-ray diffraction.

Alternatively, the catalysts may be partially crystalline. By this we mean that from 0.1 to 50% by weight of the catalyst is in the form of one or more crystalline compounds of chromium and/or one or more crystalline compounds of zinc. If a partially crystalline catalyst is used, it preferably contains from 0.2 to 25% by weight, more preferably from 0.3 to 10% by weight, still more preferably from 0.4 to 5% by weight of the catalyst in the form of one or more crystalline compounds of chromium and/or one or more crystalline compounds of zinc.

During use in a dehydrofluorination reaction the degree of crystallinity may change. Thus it is possible that a catalyst of the invention that has a degree of crystallinity as defined above before use in a dehydrofluorination reaction and will have a degree of crystallinity outside these ranges during or after use in a dehydrofluorination reaction.

The percentage of crystalline material in the catalysts of the invention can be determined by any suitable method known in the art. Suitable methods include X-ray diffraction (XRD) techniques. When X-ray diffraction is used the amount of crystalline material such as the amount of crystalline chromium oxide can be determined with reference to a known amount of graphite present in the catalyst (eg the graphite used in producing catalyst pellets) or more preferably by comparison of the intensity of the XRD patterns of the sample materials with reference materials prepared from suitable internationally recognised standards, for example NIST (National Institute of Standards and Technology) reference materials.

The zinc/chromia catalysts of the invention typically have a surface area of at least 50 m2/g and preferably from 70 to 250 m2/g and most preferably from 100 to 200 m2/g before it is subjected to pre-treatment with a fluoride containing species such as hydrogen fluoride or a fluorinated hydrocarbon. During this pre-treatment, which is described in more detail hereinafter, at least some of the oxygen atoms in the catalyst are replaced by fluorine atoms.

The zinc/chromia catalysts of the invention typically have an advantageous balance of levels of activity and selectivity. Preferably, they also have a degree of chemical robustness that means that they have a relatively long working lifetime. The catalysts of the invention preferably also have a mechanical strength that enables relatively easy handling, for example they may be charged to reactors or discharged from reactors using known techniques.

The zinc/chromia catalysts of the invention may be provided in any suitable form known in the art. For example, they may be provided in the form of pellets or granules of appropriate size for use in a fixed bed or a fluidised bed. The catalysts may be supported or unsupported. If the catalyst is supported, suitable supports include AlF3, fluorinated alumina or activated carbon.

The zinc/chromia catalysts of the invention include promoted forms of such catalysts, including those containing enhanced Lewis and/or Brönsted acidity and/or basicity.

The amorphous catalysts which may be used in the present invention can be obtained by any method known in the art for producing amorphous chromia-based catalysts. Suitable methods include co-precipitation from solutions of zinc and chromium nitrates on the addition of ammonium hydroxide. Alternatively, surface impregnation of the zinc or a compound thereof onto an amorphous chromia catalyst can be used.

Further methods for preparing the amorphous zinc/chromia catalysts include, for example, reduction of a chromium (VI) compound, for example a chromate, dichromate, in particular ammonium dichromate, to chromium (III), by zinc metal, followed by co-precipitation and washing; or mixing as solids, a chromium (VI) compound and a compound of zinc, for example zinc acetate or zinc oxalate, and heating the mixture to high temperature in order to effect reduction of the chromium (VI) compound to chromium (III) oxide and oxidise the compound of zinc to zinc oxide.

The zinc may be introduced into and/or onto the amorphous chromia catalyst in the form of a compound, for example a halide, oxyhalide, oxide or hydroxide depending at least to some extent upon the catalyst preparation technique employed. In the case where amorphous catalyst preparation is by impregnation of a chromia, halogenated chromia or chromium oxyhalide, the compound is preferably a water-soluble salt, for example a halide, nitrate or carbonate, and is employed as an aqueous solution or slurry. Alternatively, the hydroxides of zinc and chromium may be co-precipitated (for example by the use of a base such as sodium hydroxide or ammonium hydroxide) and then converted to the oxides to prepare the amorphous catalyst. Mixing and milling of an insoluble zinc compound with the basic chromia catalyst provides a further method of preparing the amorphous catalyst precursor. A method for making amorphous catalyst based on chromium oxyhalide comprises adding a compound of zinc to hydrated chromium halide.

The amount of zinc or a compound of zinc introduced to the amorphous catalyst precursor depends upon the preparation method employed. It is believed that the working catalyst has a surface containing cations of zinc located in a chromium-containing lattice, for example chromium oxide, oxyhalide, or halide lattice. Thus the amount of zinc or a compound of zinc required is generally lower for catalysts made by impregnation than for catalysts made by other methods such as co-precipitation, which also contain the zinc or a compound of zinc in non-surface locations.

Any of the aforementioned methods, or other methods, may be employed for the preparation of the amorphous catalysts which may be used in the process of the present invention.

The zinc/chromia catalysts described herein are typically stabilised by heat treatment before use such that they are stable under the environmental conditions that they are exposed to in use. This stabilisation is often a two-stage process. In the first stage, the catalyst is stabilised by heat treatment in nitrogen or a nitrogen/air environment. In the art, this stage is often called "calcination". Fluorination catalysts are then typically stabilised to hydrogen fluoride by heat treatment in hydrogen fluoride. This stage is often termed "pre-fluorination".

By careful control of the conditions under which these two heat treatment stages are conducted, crystallinity can be induced into the catalyst to a controlled degree.

For example, an amorphous catalyst may be heat treated at a temperature of from about 300 to about 600° C., preferably from about 400 to 600° C., more preferably from 500 to 590° C., for example 520, 540, 560 or 580° C. for a period of from about 1 to about 12 hours, preferably for from about 2 to about 8 hours, for example about 4 hours in a suitable atmosphere. Suitable atmospheres under which this heat treatment can be conducted include an atmosphere of nitrogen or an atmosphere having an oxygen level of from about 0.1 to about 10% v/v in nitrogen. Other oxidizing environments could alternatively be used. For example, environments containing suitable oxidizing agents include, but are not limited to, those containing a source of nitrate, CrO3 or 02 (for example air). This heat treatment stage can be conducted in addition to or instead of the calcining stage that is typically used in the prior art to produce amorphous catalysts.

Conditions for the pre-fluorination stage can be selected so that they induce a change in the crystallinity of the catalyst or so that they do not induce such a change. The present inventors have found that heat treatment of the catalyst precursor at a temperature of from about 250 to about 500° C., preferably from about 300 to about 400° C. at atmospheric or super atmospheric pressure for a period of from about 1 to about 16 hours in the presence of hydrogen fluoride, optionally in the presence of another gas such as air, can produce a catalyst in which the crystallinity is as defined above, for example from 0.1 to 8.0% by weight of the catalyst (typically from 0.1 to less than 8.0% by weight of the catalyst) is in the form of one or more crystalline compounds of chromium and/or one or more crystalline compounds of the at least one additional metal.

The skilled person will appreciate that by varying the conditions described above, such as by varying the temperature and/or time and/or atmosphere under which the heat treatment is conducted, the degree of crystallinity of the catalyst may be varied. Typically, for example, catalysts with higher degrees of crystallinity (e.g. from 8 to 50% by weight of the catalyst) may be prepared by increasing the temperature and/or increasing the calcination time and/or increasing the oxidising nature of the atmosphere under which the catalyst pre-treatment is conducted.

The variation of catalyst crystallinity as a function of calcination temperature, time and atmosphere is illustrated by the following table showing a series of experiments in which 8 g samples of a 6% zinc/chromia catalyst were subjected to calcination across a range of conditions and the level of crystallinity induced determined by X-Ray diffraction.

| Calcination Time (t, hrs) | Calcination Temperature (T, ° C.) | Atmosphere nitrogen:air (D, v/v) | % Cryst Cr2O3 Content |
| --- | --- | --- | --- |
| 4 | 400.0 | 15 | 1 |
| 4 | 400.0 | 15 | 1 |
| 2 | 450.0 | 20 | 9 |
| 6 | 350.0 | 20 | 0 |
| 2 | 450.0 | 10 | 18 |
| 2 | 350.0 | 10 | 0 |
| 6 | 450.0 | 20 | 20 |
| 6 | 350.0 | 10 | 0 |
| 6 | 450.0 | 10 | 30 |
| 4 | 400.0 | 15 | 1 |
| 2 | 350.0 | 20 | 0 |

The pre-fluorination treatment typically has the effect of lowering the surface area of the catalyst. After the pre-fluorination treatment the catalysts of the invention typically have a surface area of 20 to 200 m2/g, such as 50 to 150 m2/g, for example less than about 100 m2/g.

In use, the zinc/chromia catalyst may be regenerated or reactivated periodically by heating in air at a temperature of from about 300° C. to about 500° C. Air may be used as a mixture with an inert gas such as nitrogen or with hydrogen fluoride, which emerges hot from the catalyst treatment process and may be used directly in fluorination processes employing the reactivated catalyst.

Any catalyst used in steps (b) and (d) may be used in an amount of from about 0.01 to about 50% by weight, such as from about 0.1 to about 30%, for example from about 0.5 to about 20%, based on the weight of organics (e.g. 236ea and/or 245eb).

The (metal or carbon) catalysed dehydrofluorination of 236ea and 245eb typically is carried out at a temperature of from about 0 to about 400° C. For example, when conducted in the presence of a catalyst based on chromia (e.g. a zinc/chromia catalyst), steps (b) and (d) preferably are conducted at a temperature of from about 200 to about 360° C., such as from about 240 to about 340° C.

Steps (b) and (d) preferably are carried out at a pressure of from about 0.01 to about 25 bara or about 0.1 to about 20 bara, such as from about 1 to about 10 bara (e.g. 1 to 5 bara).

The contact time for the 236ea and/or 245eb with the catalyst in the catalysed dehydrofluorination in steps (b) and (d) suitably is from about 1 to about 500 seconds, such as from about 5 to about 400 seconds Dehydrofluorination steps (b) and (d) of the invention may be carried out in the presence of hydrogen fluoride (HF). For example, HF formed by the dehydrofluorination of 236ea and/or 245eb may be present and/or HF from a separate feed. In certain embodiments it may be desirable to use some HF in order to prevent and/or retard excessive decomposition of the organic feed and/or coking of the catalyst in steps (b) and (d). Alternatively, steps (b) and (d) may be carried out in the absence of HF and/or HF may be removed from the reactor to help drive the dehydrofluorination reaction(s).

When HF is present in step (b) and (d), the molar ratio of HF:organics (e.g. 236ea and/or 245eb) preferably is from about 0.01:1 to about 50:1, such as from about 0.1:1 to about 40:1, for example from about 0.5:1 to about 30:1 or about 2:1 to about 15:1 (e.g. from about 5:1 to about 10:1).

Another preferred method of effecting the dehydrofluorination in steps (b) and (d) is by contacting 236ea and/or 245eb with a base (base-mediated dehydrofluorination). Preferably, the base is a metal hydroxide or amide (preferably a basic metal hydroxide or amide, e.g. an alkali or alkaline earth metal hydroxide or amide).

Unless otherwise stated, as used herein, by the term "alkali metal hydroxide", we refer to a compound or mixture of compounds selected from lithium hydroxide, sodium hydroxide, potassium hydroxide, rubidium hydroxide and caesium hydroxide. Similarly, by the term "alkali metal amide", we refer to a compound or mixture of compounds selected from lithium amide, sodium amide, potassium amide, rubidium amide and caesium amide.

Unless otherwise stated, as used herein, by the term "alkaline earth metal hydroxide", we refer to a compound or mixture of compounds selected from beryllium hydroxide, magnesium hydroxide, calcium hydroxide, strontium hydroxide and barium hydroxide. Similarly, by the term "alkaline earth metal amide", we refer to a compound or mixture of compounds selected from beryllium amide, magnesium amide, calcium amide, strontium amide and barium amide.

Typically, the base-mediated dehydro-fluorination process of steps (b) and (d) is conducted at a temperature of from about −50 to about 300° C. Preferably, the process is conducted at a temperature of from about 20 to about 250° C., for example from about 50 to about 200° C. The base-mediated dehydrofluorination may be conducted at a pressure of from about 0 to about 30 bara.

The reaction time for the base-mediated dehydrofluorination process may vary over a wide range. However, the reaction time will typically be in the region of from about 0.01 to about 50 hours, such as from about 0.1 to about 30 hours, e.g. from about 1 to about 20 hours.

Of course, the skilled person will appreciate that the preferred conditions (e.g. temperature, pressure and reaction time) for conducting the base-mediated dehydrofluorination may vary depending on a number of factors such as the nature of the base being employed, and/or the presence of a catalyst etc.

The base-mediated dehydrofluorination process of steps (b) and (d) may be carried out in the presence or absence of a solvent. If no solvent is used, 236ea and/or 245eb may be passed into or over molten base or hot base, for example in a tubular reactor. If a solvent is used, in some embodiments a preferred solvent is water, although many other solvents may be used. In some embodiments solvents such as alcohols (e.g. propan-1-ol), diols (e.g. ethylene glycol) and polyols such as polyethylene glycol (e.g. PEG200 or PEG300) may be preferred. These solvents can be used alone or in combination. In further embodiments, solvents from the class known as polar aprotic solvents may be preferred. Examples of such polar aprotic solvents include diglyme, sulfolane, dimethylformamide (DMF), dioxane, acetonitrile, hexamethylphosphoramide (HMPA), dimethyl sulphoxide (DMSO) and N-methyl pyrrolidone (NMP). The boiling point of the solvent is preferably such that it does not generate excessive pressure under reaction conditions.

A preferred base is an alkali metal hydroxide selected from the group consisting of lithium hydroxide, sodium hydroxide and potassium hydroxide, more preferably, sodium hydroxide and potassium hydroxide and most preferably potassium hydroxide.

Another preferred base is an alkaline earth metal hydroxide selected from the group consisting of magnesium hydroxide and calcium hydroxide, more preferably calcium hydroxide.

The base is typically present in an amount of from 1 to 50 weight % based on the total weight of the components which make up steps (b) and (d). Preferably, the base is present in an amount of from 5 to 30 weight %.

As mentioned above, the base-mediated dehydrofluorination may preferably employ water as the solvent. Thus, the dehydrofluorination reaction may preferably use an aqueous solution of at least one base, such as an alkali (or alkaline earth) metal hydroxide, without the need for a co-solvent or diluent. However, a co-solvent or diluent can be used for example to modify the system viscosity, to act as a preferred phase for reaction by-products, or to increase thermal mass. Useful co-solvents or diluents include those that are not reactive with or negatively impact the equilibrium or kinetics of the process and include alcohols such as methanol and ethanol; diols such as ethylene glycol; ethers such as diethyl ether, dibutyl ether; esters such as methyl acetate, ethyl acetate and the like; linear, branched and cyclic alkanes such as cyclohexane, methylcyclohexane; fluorinated diluents such as hexafluoroisopropanol, perfluorotetrahydrofuran and perfluorodecalin.

The base-mediated dehydrofluorination of steps (b) and (d) is preferably conducted in the presence of a catalyst. The catalyst is preferably a phase transfer catalyst which facilitates the transfer of ionic compounds into an organic phase from, for example, a water phase. If water is used as a solvent, an aqueous or inorganic phase is present as a consequence of the alkali metal hydroxide and an organic phase is present as a result of the fluorocarbon. The phase transfer catalyst facilitates the reaction of these dissimilar components. While various phase transfer catalysts may function in different ways, their mechanism of action is not determinative of their utility in the present invention provided that they facilitate the dehydrofluorination reaction. The phase transfer catalyst can be ionic or neutral and is typically selected from the group consisting of crown ethers, onium salts, cryptands and polyalkylene glycols and derivatives thereof (e.g. fluorinated derivatives thereof).

An effective amount of the phase transfer catalyst should be used in order to effect the desired reaction, influence selectivity to the desired products or enhance the yield; such an amount can be determined by limited experimentation once the reactants, process conditions and phase transfer catalyst are selected. Typically, the amount of catalyst used relative to the amount of compound of organics in steps (b) and (d) present is from 0.001 to 20 mol %, such as from 0.01 to 10 mol %, e.g. from 0.05 to 5 mol %.

Crown ethers are cyclic molecules in which ether groups are connected by dimethylene linkages. Crown ethers form a molecular structure that is believed to be capable of receiving or holding the alkali metal ion of the hydroxide and to thereby facilitate the reaction. Particularly useful crown ethers include 18-crown-6 (especially in combination with potassium hydroxide), 15-crown-5 (especially in combination with sodium hydroxide) and 12-crown-4 (especially in combination with lithium hydroxide).

Derivatives of the above crown ethers are also useful, such as dibenzyl-18-crown-6, dicyclohexanyl-18-crown-6, dibenzyl-24-crown-8 and dibenzyl-12-crown-4. Other compounds analogous to the crown ethers and useful for the same purpose are compounds which differ by the replacement of one or more of the oxygen atoms by other kinds of donor atoms, particularly N or S. Fluorinated derivatives of all the above may also be used.

Cryptands are another class of compounds useful in the base-mediated dehydrofluorination as phase transfer catalysts. These are three dimensional polymacrocyclic chelating agents that are formed by joining bridgehead structures with chains that contain properly spaced donor atoms. The donor atoms of the bridges may all be O, N, or S, or the compounds may be mixed donor macrocycles in which the bridge strands contain combinations of such donor atoms. Suitable cryptands include bicyclic molecules that result from joining nitrogen bridgeheads with chains of (—OCH2CH2-) groups, for example as in [2.2.2]cryptand (4,7,13,16,21,24-hexaoxa-1,10-diazabicyclo[8.8.8]hexacosane, available under the brand names Kryptand 222 and Kryptofix 222).

Onium salts that may be used as catalysts in the base-mediated process of the step (iii) include quaternary phosphonium salts and quaternary ammonium salts, which may be represented by the formulae R1R2R3R4P+Z– and R1R2R3R4N+Z–, respectively. In these formulae, each of R1, R2, R3 and R4 typically represent, independently, a C1-10 alkyl group, an aryl group (e.g. phenyl, naphthyl or pyridinyl) or an arylalkyl group (e.g. benzyl or C1-10 alkyl-substituted phenyl), and Z— is a halide or other suitable counterion (e.g. hydrogen sulphate).

Specific examples of such phosphonium salts and quaternary ammonium salts include tetramethylammonium chloride, tetramethylammonium bromide, benzyltriethylammonium chloride, methyltrioctylammonium chloride (available commercially under the brands Aliquat 336 and Adogen 464), tetra-n-butylammonium chloride, tetra-n-butylammonium bromide, tetra-n-butylammonium hydrogen sulphate, tetra-n-butylphosphonium chloride, tetraphenylphosphonium bromide, tetraphenylphosphonium chloride, triphenylmethylphosphonium bromide and triphenylmethylphosphonium chloride. Benzyltriethylammonium chloride is preferred for use under strongly basic conditions.

Other useful onium salts include those exhibiting high temperature stabilities (e.g. up to about 200° C.), for example 4-dialkylaminopyridinium salts, tetraphenylarsonium chloride, bis[tris(dimethylamino)phosphine]iminium chloride and tetrakis[tris(dimethylamino)phosphinimino] phosphonium chloride. The latter two compounds are also reported to be stable in the presence of hot, concentrated sodium hydroxide and, therefore, can be particularly useful.

Polyalkylene glycol compounds useful as phase transfer catalysts may be represented by the formula R6O(R5O)mR7 wherein R5 is a C1-10 alkylene group, each of R6 and R7 are, independently H, a C1-10 alkyl group, an aryl group (e.g. phenyl, naphthyl or pyridinyl) or an arylalkyl group (e.g. benzyl or C1-10 alkyl-substituted phenyl), and m is an integer of at least 2. Preferable both R6 and R7 are the same, for example they may both by H.

Such polyalkylene glycols include diethylene glycol, triethylene glycol, tetraethylene glycol, pentaethylene glycol, hexaethylene glycol, diisopropylene glycol, dipropylene glycol, tripropylene glycol, tetrapropylene glycol and tetramethylene glycol, monoalkyl glycol ethers such as monomethyl, monoethyl, monopropyl and monobutyl ethers of such glycols, dialkyl ethers such as tetraethylene glycol dimethyl ether and pentaethylene glycol dimethyl ether, phenyl ethers, benzyl ethers of such glycols, and polyalkylene glycols such as polyethylene glycol (average molecular weight about 300) and polyethylene glycol (average molecular weight about 400) and the dialkyl (e.g. dimethyl, dipropyl, dibutyl) ethers of such polyalkylene glycols.

Combinations of phase transfer catalysts from within one of the groups described above may also be useful as well as combinations or mixtures from more than one group. Crown ethers and quaternary ammonium salts are the currently preferred groups of catalysts, for example 18-crown-6 and its fluorinated derivatives and benzyltriethylammonium chloride.

When steps (a) to (d) are carried out separately and in sequence, the product of each step may directly be reacted in the subsequent step without purification. For example, the product from step (a) containing 236ea may be fed directly to a separate reactor for the dehydrofluorination step (b). Step (b) may even be conducted in the same reactor as step (a), particularly if the same catalyst is used for steps (a) and (b).

Preferably, however, the product for each step is purified before being reacted in the subsequent step. The purification may be achieved by separation of the desired product in each step from any other products or reagents by one or more distillation, condensation or phase separation steps and/or by scrubbing with water or aqueous base. For example, the 236ea produced in step (a) may be distilled off from the hydrogen and any remaining 1216 before being fed to a reactor for dehydrofluorination step (b).

When steps (a) and (c) are carried out in the same reactor, the product from this reactor may be fed to one or more reactors to effect steps (b) and (d) without purification of the products from steps (a) and (c). Preferably, however, the 236ea and 245eb produced are separated (e.g. by distillation or any other suitable method) from the hydrogen and any remaining 1216 and 1225ye produced in steps (a) and (c) and fed to a reactor for dehydrofluorination steps (b) and (d). If steps (b) and (d) are not combined, 236ea and 245eb can be further separated from each other before passing to reactors for effecting steps (b) and (d) separately.

FIGS. 1 to 3 illustrate a preferred embodiment of the process of the invention wherein the hydrogenation steps (a) and (c) are effected continuously in the same equipment (see FIG. 1), and the dehydrofluorination steps (b) and (d) are effected continuously in the same equipment (see FIG. 2).

As shown in FIG. 1, HFP and R1225ye may be co-fed with hydrogen to a hydrogenation reactor, typically together with a recycle which serves to reduce the impact of the exotherm resulting from the hydrogenation reaction. A coolant may also be used to reduce the impact of the exotherm.

The reactor off gases may be partially condensed, with the vapour being recirculated by any suitable device (e.g. a blower, compressor or ejector) to the hydrogenation reactor inlet. The condensed liquid may then be pumped, optionally via a fluoropropane storage/pumping tank, to a distillation column (referred to in FIG. 1 as the hydrogenation stage product still).

A top fraction containing the more volatile fluoropropenes typically is recycled to the hydrogenation reactor. Optionally the operation of the hydrogenation stage product still can be adjusted to recycle a proportion of the fluoropropanes which serve to dilute the exotherm of hydrogenation reactor. A hydrogenation reactor recycle purge may also be taken and combined with the outlet of the dehydrofluorination reactor (see FIG. 2). The less volatile fluoropropane products of the hydrogenation (236ea and 245eb) may be taken from the column as a bottom fraction, either (i) as a liquid and re-vaporised, or (ii) as a vapour draw from towards the bottom the still.

As shown in FIG. 2, the vaporised products of the hydrogenation (236ea and 245eb) may be mixed with the recycle from the dehydrofluorination stage. Following heating to reaction temperature, these are fed to the dehydrofluorination reactor. If desired, the single reactor shown in the flowsheet can be replaced by two or more reactors or reaction zones, to allow optimisation of the conditions for the diverse dehydrofluorination reactions.

As mentioned above, the outlet feed from the dehydrofluorination reactor(s) may be combined with a hydrogenation reactor recycle purge before removal of HF, which is generated in, and may be present as a co-feed for, the dehydrofluorination reactor(s). Removal of HF is achieved as shown in FIG. 2 by a process scrubber, e.g. by water washing. However, other suitable methods may be used to remove HF, such as azeotropic distillation.

Following HF removal and drying (e.g. with H2SO4 in a drying tower), the crude product typically then is sent via an off-gas condenser and collections pot to a dehydrofluorination recycle still. Here, less volatile unconverted fluoropropanes are taken off from towards the bottom of the still and recycled to the reactor, and the desired fluoropropene crude product (containing 1225ye and 1234yf) is taken from the still as a top fraction.

As shown in FIG. 3, the crude fluoropropenes typically are pumped, optionally via a fluoropropene storage/pumping tank, to a first distillation column (denoted 1225ye still in FIG. 3) which removes 1225ye as a bottom fraction for recycling back to the hydrogenation reaction. A top fraction containing 1234yf is taken from the still, and may then be passed to a lights still to purify the 1234yf, e.g. by removal of any volatile components.

The invention will now be further illustrated by the following non-limiting examples.

Example 1: Hydrogenation of HFP and Z-1225ye

A tubular reactor c.a. 1.25 cm (0.5") in diameter and 20 cm long was charged with 10 g of a wet 0.5% Pd/C catalyst.

The reactor was housed inside a fan assisted oven. Thermocouples were placed at the inlet and outlet of the reactor in intimate contact with the catalyst. Once in the oven the reactor was connected to nitrogen, hydrogen and organic feeds. These feed flows were set and controlled by means of mass flow controllers.

Before use, the catalyst was first dried in a stream of nitrogen (95 ml/min) at 110° C. The catalyst was deemed to be dry when both internal thermocouples read c.a. 110° C. Next the catalyst was reduced by introducing hydrogen (5 ml/min) into the nitrogen stream and maintaining the temperature at 110° C. for 2 hours. The temperature was then increased to 150° C. for a further 30 mins.

An organic feed mixture consisting of 48.5 mol % hexafluoropropene (1216) and 51.5 mol % Z-3,3,3,2,1-pentafluoropropene (Z-1225ye) was prepared. Mixtures of this feed with hydrogen and nitrogen were then passed through the reactor and contacted with the catalyst. Samples of the gases exiting the reactor were periodically taken and analysed by GC and GC-MS. These instruments were calibrated using known standards. The results of a series of experiments with different feed compositions are shown in Table 1.

TABLE 1

| Feed flows (ml/min) | | | Inlet Temp | Reactor off-gas composition (mol %) | | | | | |
|---|---|---|---|---|---|---|---|---|---|
| N2 | H2 | Organic | (° C.) | HFP | Z1225ye | 254eb* | 245eb | 236ea | Others |
| 157.5 | 11 | 10.4 | 51 | 6.9 | 5.7 | 8.8 | 35.5 | 41.5 | 1.6 |
| 108 | 5.16 | 10.3 | 51 | 35.89 | 22.95 | 5.28 | 15.52 | 18.14 | 2.22 |
| 108 | 5.16 | 10.3 | 51 | 28.64 | 22.55 | 5.16 | 17.71 | 24.26 | 1.67 |
| 108 | 5.47 | 7.93 | 51 | 28.13 | 23.82 | 7.17 | 20.17 | 17.84 | 2.87 |
| 108 | 2.53 | 7.43 | 51 | 37.58 | 33.87 | 2.21 | 9.10 | 16.08 | 1.16 |
| 108 | 0.77 | 7.62 | 51 | 45.42 | 41.17 | 0.58 | 3.88 | 7.72 | 1.23 |

*CF3CFHCH3

Example 2: Dehydrofluorination of 236ea

A 2 g sample of an amorphous catalyst composed of 6% Zn by weight on chromia was charged to a 15 cm×1.25 mm Inconel® reaction tube installed inside a tubular furnace. This catalyst was dried at 250° C. for 1 hour then pre-fluorinated at an N2:HF ratio of 6:1 for 1 hour at 250° C. before increasing the temperature to 380° C. at which point the nitrogen diluent flow was stopped. After approximately 18 hours, the HF feed was switched off and the reactor was cooled to 220-240° C.

Following pre-fluorination, the dehydrofluorination of 236ea was studied as a function of temperature and HF:236 ratio. Feed gas flow rates were chosen so that a contact time of c.a. 5 seconds was achieved between the catalyst and feed mixture. HF:236 ratios were explored in the range 0-10. At each temperature, the system was allowed to equilibrate for about 20 minutes before reactor off-gas samples were taken at each temperature for analysis by either GC or GC-MS as described above for Example 1. The results are illustrated in Table 2.

TABLE 2

| Temperature (° C.) | Ratio HF:236ea | 236ea Conversion (%) | Z-1225ye (%) | E-1225ye (%) | Selectivity (Z + E %) |
|---|---|---|---|---|---|
| 240.0 | 0.0 | 26.5 | 24.0 | 2.2 | 99.1 |
| 260.0 | 0.0 | 42.9 | 38.2 | 4.2 | 98.8 |
| 280.0 | 0.0 | 75.8 | 65.9 | 7.9 | 97.4 |
| 300.0 | 0.0 | 89.3 | 77.0 | 10.3 | 97.7 |
| 320.0 | 0.0 | 94.7 | 80.2 | 12.1 | 97.5 |
| 240.0 | 2.5 | 3.0 | 0.1 | 0.0 | 2.7 |
| 260.0 | 2.5 | 2.8 | 0.5 | 0.1 | 19.6 |
| 280.0 | 2.5 | 5.4 | 3.2 | 0.4 | 66.7 |
| 300.0 | 2.5 | 21.2 | 17.1 | 2.1 | 90.7 |
| 320.0 | 2.5 | 56.1 | 46.8 | 6.6 | 95.3 |
| 340.0 | 2.5 | 82.2 | 67.6 | 10.6 | 95.2 |
| 360.0 | 2.5 | 90.0 | 72.2 | 11.8 | 93.4 |
| 380.0 | 2.5 | 94.0 | 73.7 | 12.6 | 91.8 |
| 240.0 | 5.0 | 2.5 | 0.0 | 0.0 | 0.8 |
| 260.0 | 5.0 | 2.3 | 0.2 | 0.0 | 7.7 |
| 280.0 | 5.0 | 2.4 | 0.8 | 0.1 | 38.5 |
| 300.0 | 5.0 | 8.2 | 4.6 | 0.6 | 63.2 |
| 320.0 | 5.0 | 23.4 | 18.0 | 2.7 | 88.1 |
| 340.0 | 5.0 | 80.0 | 63.1 | 9.5 | 90.8 |
| 360.0 | 5.0 | 90.4 | 65.3 | 10.5 | 84.4 |
| 380.0 | 5.0 | 95.9 | 49.2 | 8.0 | 59.6 |
| 240.0 | 10.0 | 0.4 | 0.1 | 0.0 | 40.5 |
| 260.0 | 10.0 | 1.2 | 1.0 | 0.1 | 93.4 |
| 280.0 | 10.0 | 5.4 | 4.1 | 0.6 | 85.9 |
| 300.0 | 10.0 | 15.2 | 13.1 | 1.6 | 96.6 |
| 320.0 | 10.0 | 56.1 | 47.7 | 6.5 | 96.7 |
| 340.0 | 10.0 | 86.3 | 70.8 | 10.8 | 94.6 |
| 360.0 | 10.0 | 91.3 | 72.8 | 11.4 | 92.1 |
| 380.0 | 10.0 | 95.7 | 73.0 | 12.5 | 89.5 |

Example 3: Dehydrofluorination of 245eb

An Inconel® reactor tube (1.25 cm (0.5")×30 cm) was charged with 6 g of a 5.2% Zn/chromia catalyst. This catalyst was pre-treated as follows before use:
Dried at 250° C. overnight under 80 ml/min nitrogen at 3 Barg
Heated to 300° C. and treated with 4 ml/min HF and 80 ml/min nitrogen at 3 Barg for 16 hrs
Nitrogen flow reduced to zero and HF flow maintained whilst continuing heating at 300° C. for a further 4 hrs
HF flow maintained and temperature increased to 380° C. at 25° C./hr
HF flow and heating at 380° C. maintained for a further 3 hrs At the end of the pre-fluorination, the reactor temperature was reduced to 310° C., the pressure reduced to 5 Barg and a mixture of HF (c.a. 1-60 ml/min) and 245eb (c.a. 30-80 ml/min) fed to the reactor. Reactor off-gas samples were periodically taken for analysis by GC and GC-MS. These instruments were calibrated with known standards. The results are presented in the Table below.

TABLE 3

| Temperature (° C.) | HF flow (ml/min) | 245eb flow (ml/min) | 245eb Conversion (%) | 245cb** yield (%) | 1234yf yield (%) |
|---|---|---|---|---|---|
| 311 | 30.68 | 0.73 | 41.29 | 15.22 | 26.1 |
| 311 | 30.85 | 0.59 | 57.21 | 24.79 | 32.4 |
| 311 | 41.49 | 9.89 | 94.49 | 53.55 | 40.8 |
| 311 | 60.19 | 37.96 | 63.74 | 18.77 | 44.95 |
| 311 | 68.43 | 50.67 | 67.39 | 16.51 | 50.89 |
| 311 | 73.92 | 55.39 | 71.55 | 17.04 | 54.51 |
| 311 | 73.89 | 55.7 | 71.69 | 16.65 | 55.03 |
| 311 | 71.88 | 54.81 | 74.02 | 17.40 | 56.59 |
| 311 | 63.67 | 40.44 | 77.96 | 19.52 | 58.44 |

**CF3CF2CH3

The invention is defined by the following claims.

We claim:

1. A process for the preparation of 2,3,3,3-tetrafluoropropene (1234yf), the process comprising:
    (a) contacting 1,1,2,3,3,3-hexafluoropropene (1216) with hydrogen in the presence of a hydrogenation catalyst to produce 1,1,2,3,3,3-hexafluoropropane (236ea);
    (b) dehydrofluorinating 236ea to produce 1,2,3,3,3-pentafluoropropene (1225ye);
    (c) contacting 1225ye with hydrogen in the presence of a hydrogenation catalyst to produce 1,2,3,3,3-pentafluoropropane (245eb); and
    (d) dehydrofluorinating 245eb to produce 1234yf;
    wherein steps (a) and (c) are carried out in vapour phase at a temperature of from about 0 to about 250° C., or from about 20 to about 200° C., or from about 50 to about 150° C.; and
    wherein the product from steps (a), (b), (c), and (d) is subjected to one or more purification steps; and
    wherein the product from steps (b) and (d) is subjected to an HF removal step and a drying step.

2. The process according to claim 1, wherein the product from steps (b) and (d) is further subjected to a distillation step.

3. The process according to claim 1, wherein the HF removal step comprises scrubbing with water or aqueous base.

4. The process according to claim 1, wherein the purification for steps (a) and (c) comprises a distillation and/or condensation step.

5. The process according to claim 1, wherein steps (a), (b), (c) and (d) are carried out sequentially in that order.

6. The process according to claim 1, wherein the HF removal step comprises scrubbing with water and aqueous base.

7. The process according to claim 1, wherein steps (b) and (d) are carried out in the vapour phase.

8. The process according to claim 1, wherein the 1225ye is stored temporarily in a buffer tank.

9. The process according to claim 1, wherein steps (b) and/or (d) are carried out in the presence of HF.

10. The process according to claim 9, wherein the molar ratio of HF:organics is from about 0.01:1 to about 50:1.

11. The process according to claim 1, wherein steps (b) and/or (d) are carried out so that HF is being removed from the reactor as it is being produced.

12. The process according to claim 1, wherein steps (b) and (d) are carried out at a temperature of from about 0 to about 400° C. and a pressure of from about 0.01 to about 25 bara or at a temperature of from about 200 to about 360° C. and a pressure of from about 1 to about 10 bara.

13. The process according to claim 1, wherein steps (b) and (d) are carried out in the presence of a catalyst comprising activated carbon, a main group metal and/or a transition metal.

14. The process according to claim 1, wherein steps (b) and (d) are carried out in the presence of a catalyst based on chromia.

15. The process according to claim 1, wherein the process is continuous or semi-continuous;
    wherein the product from steps (b) and (d) subjected to the HF removal step comprises scrubbing with water or aqueous base, followed by the drying step; and
    wherein steps (b) and (d) are carried out in a vapour phase.

16. A process for the preparation of 2,3,3,3-tetrafluoropropene (1234yf), the process comprising:
    (a) contacting 1,1,2,3,3,3-hexafluoropropene (1216) with hydrogen in the presence of a hydrogenation catalyst to produce 1,1,2,3,3,3-hexafluoropropane (236ea);
    (b) dehydrofluorinating 236ea to produce 1,2,3,3,3-pentafluoropropene (1225ye);
    (c) contacting 1225ye with hydrogen in the presence of a hydrogenation catalyst to produce 1,2,3,3,3-pentafluoropropane (245eb); and
    (d) dehydrofluorinating 245eb to produce 1234yf;
    wherein the product from steps (a), (b), (c), and (d) is subjected to one or more purification steps;
    wherein the product from steps (b) and (d) is subjected to an HF removal step and a drying step; and
    wherein the hydrogenation catalyst in step (a) and/or the hydrogenation catalyst in step (c) comprises a supported or unsupported transition metal selected from Ni, Pd, Pt, Re, Rh, Ru, and mixtures thereof and is used in an amount of from about 0.01 to about 30% by weight based on the total weight of the components which make up steps (a) and/or (c).

17. The process according to claim 16, wherein the or each hydrogenation catalyst is supported on alumina, titania, silica, zirconia or fluorides of alumina, silica, zirconia, titania, calcium fluoride, carbon and/or barium sulphate.

18. A process for the preparation of 2,3,3,3-tetrafluoropropene (1234yf), the process comprising:
    (a) contacting 1,1,2,3,3,3-hexafluoropropene (1216) with hydrogen in the presence of a hydrogenation catalyst to produce 1,1,2,3,3,3-hexafluoropropane (236ea);
    (b) dehydrofluorinating 236ea to produce 1,2,3,3,3-pentafluoropropene (1225ye);
    (c) contacting 1225ye with hydrogen in the presence of a hydrogenation catalyst to produce 1,2,3,3,3-pentafluoropropane (245eb); and
    (d) dehydrofluorinating 245eb to produce 1234yf;
    wherein steps (a) and (c) are carried out at a temperature of from about 0 to about 250° C., or from about 20 to about 200° C., or from about 50 to about 150° C.; and
    wherein the product from steps (a), (b), (c) and (d) is subjected to one or more purification steps; and
    wherein the purification for steps (b) and (d) comprises scrubbing with water or aqueous base, and a drying step; and
    wherein the purification for steps (a) and (c) comprises a distillation step; and
    wherein steps (a), (b), (c) and (d) are carried out sequentially in that order, and are carried out in the vapour phase.

* * * * *